(12) United States Patent
Hausheer

(10) Patent No.: US 6,596,320 B1
(45) Date of Patent: Jul. 22, 2003

(54) METHOD FOR TREATING CANCER HAVING GREATER EFFICACY AND REDUCED ADVERSE EFFECTS

(75) Inventor: Frederick H. Hausheer, Boerne, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 10/044,575

(22) Filed: Jan. 11, 2002

(51) Int. Cl.[7] .................. A61K 31/335; A61K 31/255; A61K 33/24
(52) U.S. Cl. .................. 424/649; 514/449; 514/517
(58) Field of Search .................. 424/649; 514/449, 514/517

(56) References Cited

U.S. PATENT DOCUMENTS 5,902,610 A * 5/1999 Hausheer et al. ........... 424/649
5,919,816 A * 7/1999 Hausheer et al. ........... 514/449

OTHER PUBLICATIONS

Carter et al., Chemotheraoy of Cancer, second edition, John Wiley & Sons, NY, NY, (1981), pp 107–108.*

* cited by examiner

Primary Examiner—Jerome D. Goldberg
(74) Attorney, Agent, or Firm—Thomas J. Dodd

(57) ABSTRACT

A method of treating patients with cancer that involves administration of a combination regimen of a platinum agent, a taxane agent, and a formula I toxicity-reducing agent. The preferred order of administration is the formula I compound, followed by the platinum complex, followed by the taxane agent.

9 Claims, No Drawings

METHOD FOR TREATING CANCER HAVING GREATER EFFICACY AND REDUCED ADVERSE EFFECTS

FIELD OF THE INVENTION

This invention relates to a method for treating patients afflicted with cancer, and will have application to a combination drug treatment possessed of fewer and less severe unwanted toxic adverse effects.

BACKGROUND OF THE INVENTION

Combination chemotherapy is a common, accepted treatment for many types of cancers. In many cases, the synergistic effects of combining two or more agents can be the difference between successful and unsuccessful treatment of the patient.

Many combination treatment regimens are well known in the oncology field. As an example, MOPP (an acronym for mechlorethamine, vincristine, procarbazine, prednisone) is a curative treatment regimen for Hodgkins' Disease. Several different combination regimens (which all include cisplatin, vinblastine and bleomycin) are accepted in the treatment of testicular cancer, which is curable in up to 98% of diagnosed cases. In all, more than 300 different combination regimens have been used.

The main drawback to combination chemotherapy is often that the synergy of action also applies to an increase in the severity, and even sometimes additional unwanted toxic effects. In addition, the schedule of administration of each drug in various combination regimens has, in many circumstance, been observed to result in greater toxicity. Particularly in cases where the preferred combination regimen includes the administration of paclitaxel followed by cisplatin, the combined effects of the two agents tends to cause dose-limiting neurotoxicity, nephrotoxicity and bone marrow suppression.

Another consideration of importance in combination chemotherapy is the sequence in which the antineoplastic agents are administered. For instance, where cisplatin and paclitaxel are administered as a part of a combination treatment regimen, it has been shown that due to severe toxicity considerations, paclitaxel must be administered first, followed by administration of cisplatin. If the order of administration is reversed, the combination is highly toxic to the patient. The anifestation of such severe schedule dependent toxicity recludes the administration of the cisplatin followed by aclitaxel combination because of the risk of serious oxicities, morbidity and even death. Currently, there is no method available to allow the safe and effective administration of cisplatin followed by paclitaxel in a combination regimen.

We have made the surprising discovery that the administration of a platinum compound (cisplatin) prior to the administration of a taxane (paclitaxel) results in at least additive antitumor activity in human cancer cells.

This invention may lead to increased antitumor activity in patients who are treated with a platinum drug followed by the administration of a taxane. The invention will allow such administration to be more safely accomplished in patients with cancer by the administration of an effective dose of a formula I compound, followed by the administration of a platinum drug, optionally followed by administration of formula I compound, definitively followed by the administration of a taxane and optionally followed by administration of formula I compound.

This new invention will result in increased antitumor activity by the sequential administration of platinum and a taxane and reduced toxicity due to the administration of a Cytoprotective agent.

Disodium 2,2'-dithiobis ethane sulfonate (also referred to in the literature as Dimesna and BNP7787) has been shown to reduce the unwanted toxic effects associated with the administration of single agent cisplatin, and of single agent paclitaxel in human patients. Dimesna is generally regarded as extremely safe and efficacious for these uses and others, and has been shown not to interfere with the cytotoxic effects of the antineoplastic agent(s) with which it is co-administered.

U.S. Pat. No. 5,919,816 and others, disclose the use of dimesna, mesna, and other related compounds to reduce the toxicity of many antineoplastic agents, as well as the toxicity of various anti-infective agents, anti-diabetic agents, and others. Other patents disclosing the use are found in the Information Disclosure Statement submitted with this application.

SUMMARY OF THE INVENTION

This invention relates to methods of treating patients with cancer by administering combination chemotherapy wherein effective amounts and schedules of administration of two or more antineoplastic agents are administered to the patient, together with a toxicity reducing amount of a protective agent of the following formula I:

$$R_1-S-X_1-R_2 \qquad (I)$$

wherein $R_1$ is hydrogen, $C_1$–$C_6$ alkyl, or —S—$X_2$—$R_3$;

$R_2$ and $R_3$ are each individually sulfonate or phosphonate; and $X_1$ and $X_2$ are each individually $C_1$–$C_6$ alkyl, optionally substituted by one or more hydroxy, sulfhydryl or alkoxy moieties.

Preferred antineoplastic agents include platinum based chemotherapy drugs (cisplatin, carboplatin, oxaliplatin, and others) and taxanes (including, but not limited to paclitaxel, docetaxel), and/or epothilones, and or vinca alkaloids, and/or oxazaphosphorines or other agents used in the chemotherapy of cancer, though the method of this invention is contemplated as useful in any of a vast number of combination chemotherapy regimens.

Dosage amounts, order of administration, routes of administration, dosage schedules, and other factors are taken into consideration when implementing the method of this invention. Some preferred schedules are set forth in the description below.

Accordingly, it is an object of this invention to provide for an improved method of treating patients with cancer for the purpose of increasing tumor shrinkage, quality of life, patient survival and the cure rate of human cancers.

Another object of this invention is to provide a new method of treating patients with cancer through combination chemotherapy along with a toxicity-preventing agent.

Another object is to provide for novel, safer, more effective methods of treating patients with cancer.

Other objects will become apparent upon a reading of the following description.

DESCRIPTION OF THE PREFERRED EMBODIMENT

The preferred embodiment herein described is not intended to be exhaustive or to limit the invention to the precise form disclosed. It is chosen and described to explain the general principles of the invention, and its application and practical use, to enable others skilled in the art to utilize and follow its teachings.

This invention involves a novel combination chemotherapy method to treat patients with cancer. By definition, combination chemotherapy involves administering two or more different antineoplastic agents using a schedule of administration to the patient that results in reduced toxicity and increased antitumor efficacy as a result of the administration of a toxicity reducing agent. The method of this invention specifically includes in addition to the antineoplastic agents, the administration of a toxicity-reducing amount of a protective agent of formula I:

$$R_1—S—X_1—R_2 \qquad (I)$$

wherein $R_1$ is hydrogen, $C_1-C_6$ alkyl, or $—S—X_2—R_3$;

$R_2$ and $R_3$ are each individually sulfonate or phosphonate; and $X_1$ and $X_2$ are each individually $C_1-C_6$ alkyl, optionally substituted by one or more hydroxy, sulfhydryl or alkoxy moieties.

The preferred protective agents of formula I include various thiols, disulfides and thioethers. Some preferred compounds of formula I include, but are not limited to mesna, dimesna, S-methyl mesna, and various analogues and derivatives of each wherein the alkylene bridge(s) include one to four $—CH_2—$ moieties, and may or may not be substituted by hydroxy or alkoxy moieties. Most preferred compounds of formula I include mesna and dimesna.

Preferred combinations of antineoplastic agents include combinations of taxanes and platinum complex agents; electrophilic alkylating agents and vinca alkaloids, oxazaphosphorines, platinum and vinca alkaloids or bleomycin, with or without steroidal antineoplastic compounds; platinum complexes and vinca alkaloids, with or without antineoplastic antibiotics; and others, some of which are shown in the following tables.

In many cases, it has been observed that the dose, the duration of drug infusion, the route of administration, and the order of administration of the antineoplastic agents can determine the outcome of treatment and to significantly affect the toxicity, drug related morbidity and death of a patient due to drug treatment. Also, the timing between doses and the duration of infusion of each agent has an effect on the safety and the efficacy outcome of treatment. As an example, the current protocol for paclitaxel/cisplatin combination therapy calls for each cycle of treatment to involve the administration of paclitaxel from 3 hours to 96 hours of the drug followed by the administration of cisplatin. Each cycle is repeated at approximately 3-week intervals.

It has been observed that the administration of cisplatin followed by paclitaxel results in an unacceptable incidence of patient toxicity that precludes its use. The inventors have discovered that the use of the toxicity reducing agents of formula I at the proper sequence can reduce or even prevent such toxicity and thereby allow greater antitumor activity from the otherwise toxic regimen.

Administration of toxicity reducing amounts and novel schedules of administration of a formula I compound in conjunction with the administration of the combination of antineoplastic agents is postulated to improve the antitumor efficacy and safety throughout the course of treatment of the patient. In many cases, adherence to the method of this invention may allow the physician to safely administer higher amounts of the antineoplastic agents, at shorter time intervals, thus improving the probability of success of a particular course of treatment.

A preferred course of treatment under the method of this invention is the administration of effective amounts of a taxane/platinum combination, in conjunction with a formula I compound. The preferred course for platinum followed by taxanes includes the administration, every 1–21 days of:

a) 10 $mg/m^2$–300 $mg/m^2$ of a platinum drug over 15 minutes to 96 hours, followed by the administration of b) 10 $mg/m^2$–400 $mg/m^2$ of a taxane; administered over 15 minutes to 96 hours; and c) 2 $g/m^2$–50 $g/m^2$ of a compound of formula I that is administered over 15 minutes to 96 hours preceding the platinum administration and the provisional administration of the formula I compound over 15 minutes to 96 hours as a single or divided dose before, during or after the administration of the taxane.

The preferred course of treatment includes the IV infusion of first, a formula I compound, followed by IV infusion of the platinum drug, followed by the administration of the taxane. This is an entirely novel schedule of platinum and taxane administration in combination with a toxicity reducing agent.

Additionally, conventional pre-medication for nausea and vomiting may be administered as per accepted medical practices.

Cisplatin is preferably administered by IV infusion over an extended period, generally from 1–12 hours, most preferably from 1–4 hours Dimesna may be administered by IV push or infusion, or may be administered orally, and is preferably administered immediately or up to 90 minutes prior to the commencement of the IV cisplatin infusion. The duration of the dimesna infusion can be from 15 minutes to continuous infusion for as long as needed to prevent toxicity.

The following specific examples are presented to disclose most preferred methods of treatment according to the method of this invention. These examples are illustrative only and are not considered as exhaustive or limiting the invention to the precise details disclosed.

EXAMPLE 1

A patient suffering from cancer is treated as follows:

a) 4 $g/m^2$–80 $g/m^2$ of dimesna is administered either by intravenous infusion over 15–90 minutes, or by oral administration route;

b) within one hour of completion of a), 15 $mg/m^2$–250 $mg/m^2$ of a platinum complex agent is administered by intravenous infusion at a rate of 0.5 mg/min–2 mg/min;

c) within 2 hours of completion of b), 20 mg/m²–250 mg/m² of a taxane agent is administered by either intravenous infusion over 15 minutes–96 hours, or by oral administration route.

EXAMPLE 2

A patient suffering from cancer is treated as follows:
a) 4 g/m²–80 g/m² of dimesna is administered either by intravenous infusion over 15–90 minutes, or by oral administration route;
b) within one hour of completion of a), 15 mg/M² –250 mg/m² of a platinum complex agent is administered by intravenous infusion at a rate of 0.5 mg/min–2 mg/min;
c) within one hour of completion of b), 4 g/m²–80 g/m² of dimesna is again administered either by intravenous infusion over 15–90 minutes, or by oral administration route;
d) within 2 hours of completion of c), 20 mg/m²–250 mg/m² of a taxane agent is administered by either intravenous infusion over 15 minutes–96 hours, or by oral administration route.

EXAMPLE 3

A patient suffering from cancer is treated as follows:
a) 4 g/m²–80 g/m² of dimesna is administered either by intravenous infusion over 15–90 minutes, or by oral administration route;
b) within one hour of completion of a), 15 mg/m²–250 mg/m² of a platinum complex agent is administered by intravenous infusion at a rate of 0.5 mg/min–2 mg/min;
c) within 24 hours of completion of b), 4 g/m²–80 g/m² of dimesna is again administered either by intravenous infusion over 15–90 minutes, or by oral administration route;
d) within 2 hours of completion of c), 20 mg/m²–250 mg/m² of a taxane agent is administered by either intravenous infusion over 15 minutes–96 hours, or by oral administration route;
e) within 2 hours of completion of d), 4 g/m²–80 g/m² of dimesna is again administered either by intravenous infusion over 15–90 minutes, or by oral administration route.

In vitro experiments were conducted to determine the efficacy of platinum/taxane combination therapy and to determine if the order of administration of the agents affected the cytotoxicity. The agents used were cisplatin (CDDP) and paclitaxel (Taxol®®), and the cell line used was MCF7/WT (breast cancer). The results of the experiments are shown below in Tables 1 and 2.

TABLE 1

Sequential Treatment of MCF7/WT
With Taxol ® followed by CDDP
MCF7/WT
2 hour-% cell survival

|  | Average | STD |
| --- | --- | --- |
| Taxol ® (27 nM) | 88 | 3 |
| CDDP (8.5 uM) | 52 | 2 |
| Taxol ® (27 nM) + CDDP (8.5 uM) | 49 | 4 |
| Taxol ® (27 nM) | 88 | 3 |
| CDDP (4.25 uM) | 73 | 1 |

TABLE 1-continued

Sequential Treatment of MCF7/WT
With Taxol ® followed by CDDP
MCF7/WT
2 hour-% cell survival

|  | Average | STD |
| --- | --- | --- |
| Taxol ® (27 nM) + CDDP (4.25 uM) | 63 | 1 |
| Taxol ® (45 nM) | 82 | 7 |
| CDDP (4.25 uM) | 73 | 1 |
| Taxol ® (45 nM ) + CDDP (4.25 uM) | 58 | 6 |
| Taxol ® (45 nM) | 82 | 7 |
| CDDP (8.5 uM) | 52 | 2 |
| Taxol ® (45 nM) + CDDP (8.5 uM) | 46 | 6 |

TABLE 2

Sequential Treatment of MCF7/WT
with CDDP followed by Taxol ®
MCF7/WT
2 hour-% cell survival

|  | Average | STD |
| --- | --- | --- |
| CDDP (4.25 uM) | 71 | 4 |
| Taxol ® (45 nM) | 45 | 1 |
| CDDP (4.25 uM) + Taxol ® (45 nM) | 26 | 5 |
| CDDP (4.25 uM) | 71 | 4 |
| Taxol ® (27 nM) | 71 | 5 |
| CDDP (4.25 uM) + Taxol ® (27 nM) | 43 | 5 |
| CDDP (8.5 uM) | 50 | 3 |
| Taxol ® (27 nM) | 71 | 5 |
| CDDP (8.5 uM) + Taxol ® (27 nM) | 27 | 3 |
| CDDP (8.5 uM) | 50 | 3 |
| Taxol ® (45 nM) | 45 | 1 |
| CDDP (8.5 uM) + Taxol ® (45 nM) | 18 | 3 |

The results of the experiments clearly elucidate at least additive cytotoxicity of the combination of platinum, then taxane, administration. Administration of a toxicity-reducing amount (4 g/m²–80 g/m²) of the formula I compound in the manner described above will reduce the unwanted toxicity of this combination and route to render the combination relatively safe and effective for administration to mammalian subjects, particularly to human subjects.

I claim:
1. A method for treating a patient with cancer comprising administering an effective, synergistic amount of the following combination of agents to said patient:
   a) 4 g/m²–80 g/m² of a compound of formula I:

$$R_1-S-X_1-R_2 \tag{I}$$

wherein $R_1$ is hydrogen, $C_1-C_6$ alkyl, or $-S-X_2-R_3$;
   $R_2$ and $R_3$ are each individually sulfonate or phosphonate; and
   $X_1$ and $X_2$ are each individually $C_1-C_6$ alkyl, optionally substituted by one or more hydroxy, sulfhydryl or alkoxy moieties; then administering
   b) 10 mg/m²–300 mg/m² of a platinum complex by infusion; then administering
   c) 20 mg/m²–300 mg/m² of a taxane antineoplastic agent.
2. The method of claim 1 wherein said taxane is paclitaxel, said platinum complex is cisplatin and said formula I compound is dimesna.

3. The method of claim 2 wherein the combination of agents is administered to the patient once a week.

4. The method of claim 2 wherein the combination of agents is administered to the patient daily.

5. The method of claim 2 wherein the combination of agents is administered to the patient biweekly.

6. The method of claim 2 wherein the combination of agents is administered to the patient once every 21 days.

7. The method of claim 2 wherein the combination of agents is administered to the patient by IV infusion.

8. The method of claim 1 wherein step a) is repeated after step b).

9. The method of claim 8 wherein step a) is again repeated after step c).

* * * * *